United States Patent [19]

Meyer, Jr. et al.

[11] Patent Number: 4,861,579
[45] Date of Patent: Aug. 29, 1989

[54] SUPPRESSION OF B-LYMPHOCYTES IN MAMMALS BY ADMINISTRATION OF ANTI-B-LYMPHOCYTE ANTIBODIES

[75] Inventors: Harry M. Meyer, Jr., Mahwah; Martin J. Weiss, Fort Lee, both of N.J.

[73] Assignee: American Cyanamid Company, Stamford, Conn.

[21] Appl. No.: 169,263

[22] Filed: Mar. 17, 1988

[51] Int. Cl.$^4$ .................... A61K 43/00; A61K 49/00; A61K 39/395
[52] U.S. Cl. ......................................... 424/1.1; 424/9; 424/85.91; 530/387; 514/2
[58] Field of Search .......................... 424/1.1, 9, 85.91; 530/387, 902; 514/2, 21

[56]  References Cited

U.S. PATENT DOCUMENTS 4,500,508  2/1985  Srivastave et al. .................. 424/1.1

Primary Examiner—John S. Maples
Attorney, Agent, or Firm—H. G. Jackson

[57]  ABSTRACT

Selective suppression of B-lymphocytes in mammals is accomplished by treatment with an adequate amount of antibody to a mature B-lymphocyte surface marker.

12 Claims, No Drawings

SUPPRESSION OF B-LYMPHOCYTES IN
MAMMALS BY ADMINISTRATION OF
ANTI-B-LYMPHOCYTE ANTIBODIES

BACKGROUND OF THE INVENTION

The site-selective delivery of cytotoxic agents, radionuclides, toxins or pro-flammatory substances to tumors by conjugation of these agents to monoclonal antibodies specific for tumor-associated antigens offers the promise of important advances in cancer diagnosis and therapy. At present the use of human antibodies is limited and therapeutic and diagnostic applications are not practical. Therefore, it is necessary to resort to antibodies derived from appropriate animals—usually the mouse. Since these antibodies are foreign to the human, an immune response is to be expected and indeed is often noted as discussed by J. W. Larrick and J. M. Bourla in Prospects for the Therapeutic Use of Human Monoclonal Antibodies, *J. Biol. Responses Modifiers*, 5, 379–393 (1986).

Moreover, antibodies may be formed in response to foreign proteins (e.g. toxins) coupled to the therapeutic antibody. Even with human or chimeric (human constant plus mouse variable regions) antibodies an immune response is a possibility. This response involves the formation by the host's B-lymphocytes of antibodies to the administered antibodies or other foreign proteins as discussed by R. C. Kennedy et al in *Scientific American*, 225, 48 (1986). When they occur, such responses compromise the therapeutic approach since they neutralize the therapeutic antibody before it has had the opportunity to carry out its function. In addition, there is also the possibility of serious hypersensitivity reactions which may endanger the patient as discussed by L. Chatenoud in The Immune Response Against Therapeutic Antibodies, *Immunology Today*, 7, 367–368 (1986) and M. L. Zoler in Monoclonal Antibodies: On the Verge of Therapeutic Reality? *Medical World News*, 92–108, June 9, 1986. In order to minimize the immune response, a mammal can be treated with a variety of known immunosuppressive agents, alone or in combination, such as corticosteroids, cyclosporin, cyclophosphamide and others. These agents, although partially effective, are non-selective and generally suppress many components of the immune system and consequently to obtain the desired suppression of the mammal's humoral response, serious and even life-threatening side-effects can occur as a result of the concomitant action against other immune system components. This invention provides a novel, specific and therefore more preferable procedure to temporarily suppress that component, and only that component, of the immune system which is responsible for the antibody response to foreign proteins, such as murine-derived antibodies, namely the B-lymphocytes.

SUMMARY OF THE INVENTION

The invention is a therapeutic method which comprises administration to a mammal of a pharmaceutically effective amount(s) of one or more anti B-lymphocyte antibodies or fragments thereof, unmodified or conjugated to an appropriate radioisotope, cytotoxic agent or toxin or altered to elicit antibody mediated or cell mediated cytotoxicity. The antibody is administered in an amount sufficient to suppress the response of the B-lymphocytes to concurrent, subsequent, or prior administration to the mammal of diagnostic or therapeutic doses of, unmodified antibodies or antibody fragments, or conjugates thereof with therapeutic or diagnostic agents such as radioisotopes, toxins, cytotoxic agents, or the like; or to other therapeutic or diagnostic non-antibody foreign proteins. The invention includes immunosuppressive formulations. The invention also includes immunosuppressive diagnostic and therapeutic formulations.

DESCRIPTION OF THE PREFERRED EMBODIMENTS

The invention is a method to suppress the response of B-lymphocytes in mammals to diagnostic or therapeutic doses of unmodified antibodies, antibody fragments or conjugates thereof with radioisotopes, toxins or cytotoxic agents or other diagnostic or therapeutic doses of non-antibody foreign proteins comprising administering to a mammal one or more anti B-lymphocyte unmodified antibodies or fragments thereof or anti B-lymphocyte antibodies or fragments thereof conjugated to a radioisotope, cytotoxic agent or toxin or anti B-lymphocyte antibodies or fragments thereof altered to elicit antibody or cell mediated cytotoxicity in a pharmaceutically effective amount to suppress the response of the B-lymphocytes to concurrent, subsequent or prior administration to the mammal of effective doses of diagnostic or therapeutic unmodified antibodies, antibody fragments or conjugates thereof with radioisotopes, toxins or cytotoxic agents diagnostic or therapeutic doses of non-antibody foreign proteins.

The invention includes an immunosuppressive formulation comprising one or more anti B-lymphocyte unmodified antibody or fragments thereof or anti B-lymphocyte antibodies or fragments thereof conjugated to a radioisotope, cytotoxic agent or toxin or anti B-lymphocyte antibodies or fragments thereof altered to elicit antibody or cell mediated cytotoxicity and a pharmaceutically suitable carrier.

The invention further includes immunosuppressive diagnostic or therapeutic formulations comprising diagnostic or therapeutic unmodified antibodies, antibody fragments or conjugates thereof with radioisotopes, toxins or cytotoxic agents; or diagnostic or therapeutic non-antibody proteins and and immunosuppressive anti B-lymphocyte unmodified antibodies or fragments thereof or anti B-lymphocyte antibodies or fragments thereof conjugated to a radioisotope, cytotoxic agent or toxin or anti B-lymphocyte antibodies or fragments thereof altered to elicit antibody or cell mediated cytotoxicity and a pharmaceutically suitable carrier.

Selective suppression of the B-lymphocytes can be accomplished by treatment with an adequate amount of antibody to a mature B-lymphocyte surface marker. Preferably, this antibody should recognize the mature B-lymphocyte and not the stem cell, thus allowing for a later repopulation of B-lymphocytes by the stem cell. Such antibodies can be prepared readily by procedures well-known in the art. Antibodies to malignant B-lymphocytes, useful for the treatment of B-lymphocyte lymphoma, are often cross-reactive with normal B-lymphocytes and also can be used for this purpose. Examples of such antibodies exist in the literature. For example, Epstein and co-workers describe the preparation of two such antibodies, termed Lym-1 and Lym-2, in *Two New Monoclonal Antibodies, Lym-1 and Lym-2, Reactive with Human B-Lymphocytes and Derived Tumors, with Immunodiagnostic and Immunotherapeutic Potential,*

*Cancer Research,* 47, 830–840 (1987); also note references cited in this paper to other anti B-lymphocyte antibodies. Although these antibodies are of murine origin their repeated administration to humans is not precluded since the B-lymphocyte response to their murine aspect will be suppressed. Since it is possible that in some, if not in many or all cases, the B-lymphocyte population may not all share the same surface marker, it may be necessary to utilize more than one antibody to effectively achieve the desired suppression of the B-lymphocyte response. This invention envisions the utilization of as many antibodies as necessary to accomplish this goal.

This invention envisions the use of unmodified ("naked") antibodies as well as antibodies conjugated with a suitable cytotoxic agent, toxin or radionuclide. Appropriate radioisotopes include $^{131}$I, $^{90}$Y, and $^{67}$Cu. Procedures for the preparation of iodinated antibodies are well-known in the art (see S. L. Mills et al., *Hybridoma,* 5, 265–275 (1986) and references cited therein) and such preparations can be carried out easily in hospital radiopharmacies. [For $^{90}$Y see L. C. Washburn et al., *Nucl. Med. Biol.* 13, 453–456 (1986) and M. Chinol Md D. J. Hnatowich *J. Nucl. Med.,* 28, 1465–1470 (1987) and for $^{67}$Cu see M. K. Moi et al., *Analytical Biochemistry,* 148, 249–253 (1985)]. For the purposes of this invention a preparation containing on average about one alpha or beta-emitting radioisotope for each antibody molecule would be preferred.

The antibody also can be conjugated, by procedures described in the art with known cytotoxic drugs such as methotrexate, aminopterin, mitoxantrone, vincristine, vinblastine, doxorubicin and others, or with plant toxins such as abrin, or ricin or the like or their ribosome-inactivating sub-units, or any other agents known to have cytotoxic properties.

In addition, this invention contemplates the use of genetically, enzymatically, or chemically altered antibodies which recognize B-lymphocytes, whereby the constant regions have been altered or replaced with domains which fix complement proteins or elicit target cell destruction by virtue of antibody-dependent cellular cytotoxicity (ADCC), thus activating the patient's own immune system.

In addition to cancer therapy, this novel modality would be similarly useful in conjunction with the use of therapeutic monoclonal antibodies in the treatment of diseases such as bacterial, viral, protozoal and other infections, endotoxic shock, autoimmune diseases, progressive multiple sclerosis and others. In the instance of organ transplant rejection, treatment with the murine-derived anti-T lymphocyte OKT-3 antibody is accompanied by a strong B-lymphocyte response to the mouse antibody, which, at least in part, compromises this approved clinically-useful procedure [C. F. Shield II et al., *Nephron* 46: suppl. 1, 48–51 (1987)]. Use of the modality of this invention in conjunction with OKT-3 antibody and the like would enhance the efficiency of this procedure.

EXAMPLE 1

An immunosuppresive formulation of Lym-1 antibody capable of suppressing the response of B-lymphocytes and a pharmaceutically suitable carrier (Example 9) is administered to a mammal. Following the method of treatment of this example should result in the selective suppression of B-lymphocytes.

EXAMPLE 2

An immunosuppressive formulation of $^{131}$I-Lym-1 in a pharmaceutically acceptable carrier (Example 8) is administered to a mammal. Following the method of treatment of this example should result in the selective suppression of B-lymphocytes allowing the administration of multiple doses of murine-derived antibodies for therapeutic purposes.

EXAMPLE 3

An immunosuppresive formulation of $^{131}$I-Lym-1 in a pharmaceutically acceptable carrier (Example 8) is administered to a mammal. Following the method of treatment of this example should result in the selective suppression of B-lymphocytes allowing the administration of multiple doses of therapeutic antibody conjugated to ricin A-chain.

EXAMPLE 4

An immunosuppressive formulation of $^{131}$I-Lym-1 in a pharmaceutically acceptable carrier (Example 8) is administered to a mammal. Following the method of treatment of this example should result in the selective suppression of B-lymphocytes allowing the administration of multiple doses of therapeutic antibody conjugated to a derivative of vinblastin, vincristine or vindesin.

EXAMPLE 5

A site-selective formulation of a therapeutic dose of antibody conjugated with methotrexate in a pharmaceutically suitable carrier is administered to a mammal. Then $^{131}$I-Lym-1 antibody in a pharmaceutically suitable carrier (Example 8) is administered to the same mammal. Following the method of treatment of this example should result in the site-selective delivery of the cytotoxic agent and the selective suppression of B-lymphocytes.

EXAMPLE 6

A formulation containing murine derived anti-T cell OKT-3 antibody is administered to a mammal after an organ transplant. Then $^{131}$I-Lym-1 antibody in a suitable carrier (Example 8) is administered to the same mammal. Following the method of treatment of this example should enhance the efficiency of the OKT-3 antibody treatment.

EXAMPLE 7

A formulation containing murine derived anti-T cell OKT-3 antibody is administered to a mammal after an organ transplant while concurrently administering $^{131}$I-Lym-2 antibody (prepared in the manner of Example 8) in a suitable carrier to the same mammal. Following the method of treatment of this example should enhance the efficiency of the OKT-3 antibody treatment.

EXAMPLE 8

Iodination Procedure Preparation of $^{131}$I-Lym Dosage Formulation

1. All containers, chromatographic media, and tubing required for the procedure are sterilized.
2. Adjust Na$^{131}$I solution to pH of about 8.5 by addition of 0.1N HCl.
3. Centrifuge monoclonal antibody LYM-1 for injection.

4. Add LYM-1 to Na$^{131}$I solution at one to one molar ratio.

5. Add chloramine-T solution at a ratio of 1.25 mcg chloramine-T to 100 mcg LYM-1 and vortex.

6. React at 4° C. for 10 minutes.

7. Quench reaction by addition of a sodium metabisulfite solution (at 2 to 1 molar ratio to chloramine-T).

8. Chromatograph on Biogel P-10/Dowex 1-X8 column.

9. Pass through a 0.2 micron filter.

10. Collect in a 50 ml vial; adjust $^{131}$I activity to about 150 millicuries by withdrawal of excess solution; dulute to 50 ml with a phosphate buffered saline solution containing 5% human serum albumin.

A pharmaceutically suitable carrier for the formulations of this invention is sterile phosphate-buffered saline optionally containing about 5% human serum albumin, for example, see Example 9.

EXAMPLE 9

LYM-1 FORMULATION COMPOSITION

| Component | Percent (w/w) | Quantity per Unit Dose (mg/10 ml) |
|---|---|---|
| LYM-1 | 1.0 | 10.0 |
| Sodium Phosphate, Monobasic USP | 0.022* | 0.22* |
| Sodium Phosphate, Dibasic USP | 0.119* | 1.19* |
| Sodium Chloride USP | 0.877 | 8.77 |
| Hydrochloric Acid USP or Sodium Hydroxide USP | ** | ** |
| Water for Injection qs ad v | — | 10 ml |

*Anhydrous basis.
**Added to adjust pH to approximately 7.2

We claim:

1. A method to suppress the response of B-lymphocytes in mammals to diagnostic or therapeutic doses of unmodified antibodies or antibody fragments; or of conjugates thereof with radioisotopes, toxins or cytotoxic agents; or of diagnostic or therapeutic doses of non-antibody foreign proteins comprising
administering to a mammal one or more
anti B-lymphocyte unmodified antibodies or fragments thereof or
anti B-lymphocyte antibodies or fragments thereof conjugated to a radioisotope, cytotoxic agent or toxin or
anti B-lymphocyte antibodies or fragments thereof altered to elicit antibody or cell mediated cytotoxicity
in a pharmaceutically effective amount to suppress the response of the B-lymphocytes to concurrent, subsequent, or prior administration to the mammal of effective doses of the diagnostic or therapeutic unmodified antibodies, antibody fragments or conjugates thereof with radioisotopes, toxins or cytotoxic agents; or the diagnostic or therapeutic doses of non-antibody foreign proteins.

2. A method to suppress the response of B-lymphocytes in mammals to diagnostic or therapeutic doses of unmodified antibodies or antibody fragments; or of conjugates thereof with radioisotopes, toxins or cytotoxic agents; or of diagnostic or therapeutic doses of non-antibody foreign proteins according to claim 1 comprising
administering to a mammal one or more
anti B-lymphocyte unmodified antibodies or fragments thereof
in a pharmaceutically effective amount to suppress the response of the B-lymphocytes to subsequent, concurrent, or prior administration to the mammal of effective doses of the diagnostic or therapeutic unmodified antibodies, antibody fragments or conjugates thereof with radioisotopes, toxins or cytotoxic agents; or of diagnostic or therapeutic doses of non-antibody foreign proteins.

3. A method according to claim 2 wherein the anti B-lymphocyte antibody is Lym-1 or Lym-2.

4. A method according to claim 2 wherein the anti B-lymphocyte antibodies are Lym-1 and Lym-2.

5. A method to suppress the response of B-lymphocytes in mammals to diagnostic or therapeutic doses of unmodified antibodies or antibody fragments; or of conjugates thereof with radioisotopes, toxins or cytotoxic agents; or of diagnostic or therapeutic doses of non-antibody foreign proteins according to claim 1 comprising
administering to a mammal one or more
anti B-lymphocyte antibodies or fragments thereof conjugated to a
radioisotope, cytotoxic agent or toxin
in a pharmaceutically effective amount to suppress the response of the B-lymphocytes to subsequent administration to the mammal of effective doses of the diagnostic or therapeutic unmodified antibodies or antibody fragments; or of conjugates thereof with radioisotopes, toxins or cytotoxic agents; or of the diagnostic or therapeutic doses of non-antibody foreign proteins.

6. A method according to claim 5 wherein the anti B-lymphocyte antibody is Lym-1 or Lym-2 conjugated to $^{131}$I.

7. A method according to claim 5 wherein the anti B-lymphocyte antibodies are Lym-1 and Lym-2, each conjugated to $^{131}$I.

8. The method according to claim 5 wherein the therapeutic antibody is an anti-melanoma antibody conjugated to the ricin A-chain.

9. A method to suppress the response of B-lymphocytes in mammals to diagnostic or therapeutic doses of unmodified antibodies or antibody fragments; or of conjugates thereof with radioisotopes, toxins or cytotoxic agents; or of diagnostic or therapeutic doses of non-antibody foreign proteins according to claim 1 comprising
administering to a mammal one or more
anti B-lymphocyte antibodies or fragments thereof altered to elicit antibody or cell mediated cytotoxicity
in a pharmaceutically effective amount to suppress the response of the B-lymphocytes to subsequent, concurrent or prior administration to the mammal of effective doses of the diagnostic or therapeutic unmodified antibodies, antibody fragments or conjugates thereof with radioisotopes, toxins or cytotoxic agents; or of the diagnostic or therapeutic doses of non-antibody foreign proteins.

10. A method to suppress the response of B-lymphocytes in mammals to multiple therapeutic doses of anti T-lymphocyte antibody according to claim 1.

11. A method according to claim 10 wherein the anti T-lymphocyte antibody is the OKT-3 antibody and the anti B-lymphocyte antibody is Lym-1 or Lym-2 conjugated to $^{131}$I.

12. A method according to claim 10 wherein the anti T-lymphocyte antibody is OKT-3 antibody and the anti B-lymphocyte antibodies are Lym-1 and Lym-2 each conjugated to $^{131}$I.

* * * * *